United States Patent [19]

Sueptitz

[11] Patent Number: Plant 7,042

[45] Date of Patent: Sep. 26, 1989

[54] CHRYSANTHEMUM PLANT NAMED MAXIMO

[75] Inventor: Dieter Sueptitz, Hamburg, Fed. Rep. of Germany

[73] Assignee: Ball Seed Company, Chicago, Ill.

[21] Appl. No.: 170,450

[22] Filed: Mar. 18, 1988

[51] Int. Cl.[4] ..... A01H 5/00
[52] U.S. Cl. ..... Plt./74
[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Maximo having anemone flower form, white ray florets, tubular inner portions opening up to a flat apex, funnelform deep disc florets which are bright yellow when mature, nine week response, vigorous growth habit, high productivity of flowers per stem, dark green deeply lobed foliage, and the ability to perform well under low light, cool temperature conditions.

1 Drawing Sheet

The present invention comprises a new and distinct cultivar of Chrysanthemum plant, botanically known as *Dendranthema grandiflora,* and hereinafter referred to by the cultivar name Maximo.

Maximo is a product of a planned breeding program which had the objective of creating new Chrysanthemum cultivars having a vigorous growth habit, long stems and peduncles, anemone type flowers and excellent keeping qualities, making it suitable for use as a cut flower. Such traits in combination were not present or needed improvement in previously available commercial cultivars.

Maximo was originated from a hybridization made by applicant in a controlled breeding program in Hamburg, Federal Republic of Germany, in 1977. The female parent of Maximo Seedling No. 75136 and the male parent was Seedling No. 73390. Maximo was discovered and selected as one flowering plant within the progeny of the stated parentage by applicant in June, 1977 in a controlled environment in Hamburg, Germany.

The first act of asexual reproduction of Maximo was accomplished when vegetative cuttings were taken from the initial selection in January, 1978 in a controlled environment in Hamburg, Federal Republic of Germany by a technician working under formulations established and supervised by applicant. Horticultural examination of selected units initiated in April, 1978 has demonstrated that the combination of characteristics as herein disclosed for Maximo are firmly fixed and are retained through successive generations of asexual reproduction.

Maximo has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Maximo, which in combination distinguish this Chrysanthemum as a new and distinct cultivar:

1. Anemone type flower form.

2. White ray florets with bright yellow mature disc florets which are yellow green at the unopened, immature stage.
3. From the base to about half the length of the ray florets, the margins are fused forming a tube, with the outer half opening up and the apex of the floret being flat.
4. Disc florets are funnel shaped and up to 18 mm long.
5. Very vigorous growth habit, making Maximo suitable for use as a cut flower.
6. Highly productive, having many flowers per stem.
7. Dark green, sharply toothed foliage which is medium to small in size when compared to other cut type Chrysanthemum varieties.
8. Nine week flower response.
9. Performs well under low light, cool temperature conditions.

Of the many commercial cultivars known to the present inventor, the most similar in comparison to Maximo is Tree Lane. Reference is made to Chart A which compares certain characteristics of Maximo to those same characteristics of Tree Lane. In comparison to Tree Lane, Maximo has more sharply toothed foliage, a more vigorous growth habit, a darker yellow and larger disc, and the disc does not display a "dark eye" when grown under cool temperatures as Tree Lane does. The flower type and diameter, ray floret color, and number of ray florets of Maximo are similar to those same characteristics of Tree Lane.

The accompanying photographic drawing shows typical inflorescence and foliage characteristics of Maximo, with colors being as nearly true as possible with illustrations of this type. Sheet 1 is a black and white photograph with one flower and a few leaves being colored to accurately depict true flower and foliage color.

In the following description, color references are made to The Royal Horticultural Society Colour Chart. The color values were determined between 3:00 and 3:30 p.m. on Dec. 30, 1987 under fluorescent lighting at Parrish, Fla.

Classification:

*Botanical.—Dendranthema grandiflora,* cv. Maximo.

*Commercial.*—Cut anemone spray.

INFLORESCENCE

A. Capitulum:
*Form.*—Flat.
*Type.*—Anemone.
*Diameter across face.*—6–7.5 cm.

B. Corolla of ray florets:
*Color (general tonality from a distance of three meters).*—White.
*Color (upper surface).*—155D.
*Color (under surface).*—155D.

C. Corolla of disc florets:
*Color (mature).*—5A.
*Color (immature).*—Yellow-green 149B.

D. Reproductive organs:
*Androecium.*—Present in disc florets only.
*Gynoecium.*—Present in both disc and ray florets.

PLANT

A. General appearance:
*Height.*—95 cm when grown unpinched and given 2 weeks of long days before short days begin.

B. Foliage:
*Color (upper surface).*—147A.

*Color (under surface).*—147B.
*Shape.*—Ovate, deeply lobed and serrated.

CHART A

| | Maximo | Tree Lane |
|---|---|---|
| Flower diameter | 6 cm–7.5 cm | 6 cm–7.5 cm |
| Average number of ray florets | 33.5 | 33.4 |
| Height of flowering plant given 2 weeks of long days | 95 cm | 70 cm |
| Fully expanded ray floret width | 7–8.5 mm | 7–8 mm |
| Fully expanded ray floret length | 31–35 mm | 26–32 mm |
| Flower response after onset of short days | 9 weeks | 8.5 weeks |
| Ray floret color | 155D | 155D |
| Diameter of disc | 34–38 mm | 29–33 mm |
| Mature disc floret color | 5A | 4C |
| Disc floret length | 12–18 mm | 10–14 mm |

I claim:

1. A new and distinct cultivar of Chrysanthemum plant named Maximo, as illustrated and described, and parts thereof.

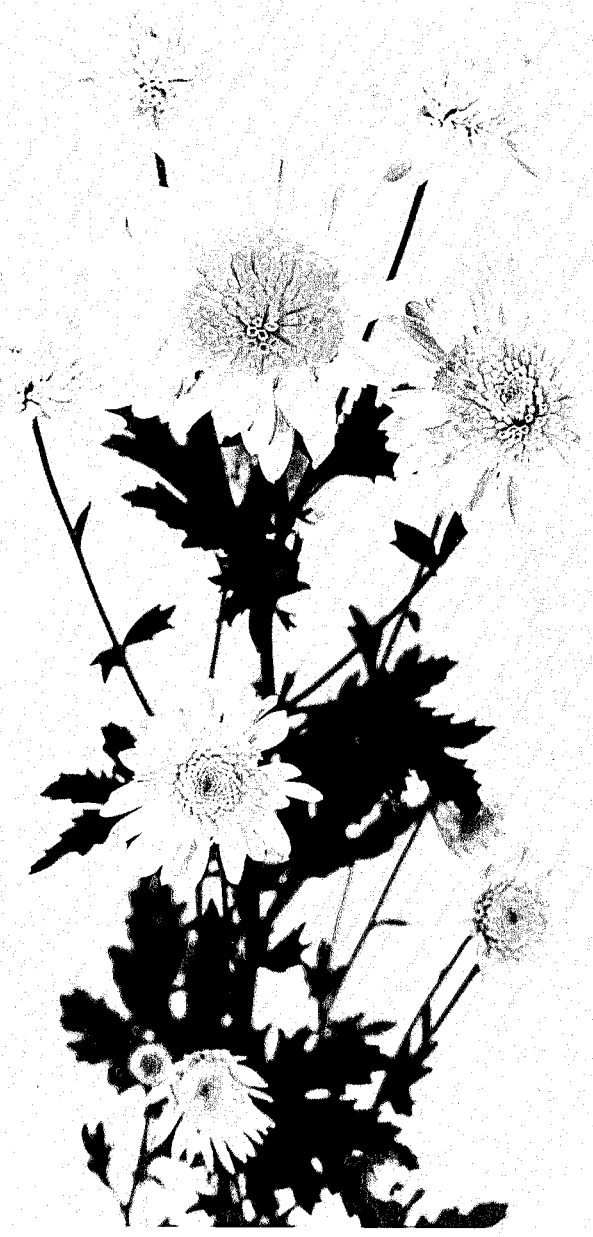

* * * * *